United States Patent [19]

Grubbs et al.

[11] Patent Number: 4,690,992

[45] Date of Patent: Sep. 1, 1987

[54] POLYMERIZATION OF DIFUNCTIONAL RING COMPOUNDS

[75] Inventors: Robert H. Grubbs; Laura R. Gilliom, both of Pasadena, Calif.; Alain Siove, Paris, France

[73] Assignee: California Institute of Technology, Pasadena, Calif.

[21] Appl. No.: 855,370

[22] Filed: Apr. 24, 1986

Related U.S. Application Data

[62] Division of Ser. No. 594,355, Mar. 28, 1984, Pat. No. 4,607,112.

[51] Int. Cl.$^4$ ............................................. C08F 4/64
[52] U.S. Cl. .................................... 526/160; 526/170
[58] Field of Search ............................ 526/160, 170

[56] References Cited

U.S. PATENT DOCUMENTS

| | | | |
|---|---|---|---|
| 4,542,199 | 9/1985 | Kaminsky | 526/160 |
| 4,567,244 | 1/1986 | Grubbs | 526/160 |
| 4,588,794 | 5/1986 | Oda | 526/283 |

Primary Examiner—Paul R. Michl

Attorney, Agent, or Firm—Marvin E. Jacobs

[57] ABSTRACT

A difunctional monomer containing a strained olefin ring and an unstrained olefin, ether group or other group polymerizable with Lewis acid or Ziegler-Natta coordination catalyst by forming a complex of the monomer and $Cp_2TiCH_2$ (Cp is $\eta^5$—$C_5H_5$) and heating the complex in presence of excess monomer to above the decomposition point. A controlled, selective opening of the ring with the strained olefin occurs to form a linear, soluble polymer having the non-polymerized group pendant from the chain. An improved catalyst is formed by preparing the catalyst with a base such as 4-dimethylaminopyridine that forms an insoluble adduct with $AlR_2Cl$ which is precipitated and removed. Aluminum can also be eliminated by using a precursor of the formula:

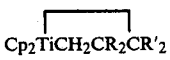

$$Cp_2TiCH_2CR_2CR'_2 \qquad (5)$$

When compound (5) is reacted with monomer, the catalyst-monomer complex forms by elimination of a volatile component (isobutylene when $R^1$ is Me and R is H) which is removed by venting.

12 Claims, No Drawings

POLYMERIZATION OF DIFUNCTIONAL RING COMPOUNDS

This is a division of application Ser. No. 594,355, filed on Mar. 28, 1984, now U.S. Pat. No. 4,607,112.

ORIGIN OF THE INVENTION

The invention described herein was made in the performance of work under contracts with the National Science Foundation and is subject to the provisions of the National Science Foundation Act Under National Science Foundation Grant No. CHE8214668.

BACKGROUND OF THE INVENTION

The invention relates to the polymerization of ring compounds and, more particularly, to the selective ring-opening polymerization of ring compounds containing a strained double bond and at least one other potentially polymerizable group or site.

DESCRIPTION OF THE PRIOR ART

Numerous catalysts are known for the ring-opening polymerization of cyclic olefins. A wide variety of transition metal salt catalysts such as tungsten, molybdenum and rhenium have been reported for use in general ring opening polymerization. However, the catalysts require the presence of a co-catalyst and none of these catalysts display selectivity for strained unsaturated bonds over other potentially reactive functionalities. Diolefin monomers are polymerized to high molecular weight, insoluble, intractable masses and/or to polymers having wide dispersions of molecular weights. The dispersity of these polymers can be as low as 4, but usually is in the range from 10-20. These catalysts are Lewis acids which are reactive with oxygen substitution or ether linkages and cannot be used with oxygen-containing monomers.

The "Tebbe" reagent, $[\eta^5-C_5H_5]TiCH_2 \cdot AlClMe_2$, has been shown to react with olefins in the presence of pyridine to form titanacyclobutanes. The latter have been shown capable of functioning as intermediates in olefin metathesis [T. R. Howard, et al., *J. Am. Chem. Soc.*, 102, 6876 (1980)]. Howard, Grubbs and Marchand (Southeast/Southwest Regional Meeting of ACS, Program Abstracts, Dec. 10, 1980) report the reaction of norbornene with the Tebbe reagent in the presence of pyridine to form a titanacyclobutane intermediate which can be used to promote ring-opening polymerization of norbornene. The polymer is not identified nor is there any indication of selectivity between strained rings and other functionalities. During catalyst preparation, the dimethylaluminum moiety of the Tebbe reagent is eliminated by reaction with pyridine. Some appears to remain as an impurity in the resulting polymer.

Dicyslopentadiene is a by-product of petroleum refining available from cracking. There has been considerable research effort expended on developing a catalyst capable of forming lower molecular weight products with narrower distribution of molecular weight, since this monomer is so readily available and theoretically is capable of forming good elastomers. However, since all the prior art catalysts are not selective, both rings react and the molecular weight of the polymer is too high and the polymer too intractable for commercial use. Other readily available monomers containing reactive base Lewis groups, such as ethers, would also be desirable for the preparation of new materials.

STATEMENT OF THE INVENTION

A polymerization system for the selective ring-opening polymerization of a strained olefin has been developed in accordance with the invention. The catalyst used in the invention is unreactive with oxygen containing groups and with unstrained olefins. The catalyst is a one-component catalyst that is readily prepared and removed from the polymer. The work up and clean up of the polymer are much easier than the Lewis acid or Ziegler-Natta type catalysts previously utilized for ring-opening polymerization. The resulting polymers have much lower molecular weight, are substantially soluble in common solvents and have a reasonably narrow distribution of molecular weight.

The invention also relates to an improved method of preparing the catalyst in presence of a base which forms an insoluble adduct with the by-product of the catalyst dissociation. An active catalyst has also been formed that does not contain any aluminum. This catalyst emits a volatile by-product which further simplified polymerization and recovery of the polymer.

Yields up to 60% of polymers having solubility up to 80% are possible utilizing the polymerization system of the invention. It has also been discovered that yields are increased at higher temperatures but with substantial decrease in the soluble fraction.

In the polymerization system of the invention a complex precursor of $Cp_2TiCH_2$ (Cp is $\eta^5-C_5H_5$) and a monomer containing a strained olefin and another group polymerizable by Lewis acid or Ziegler-Natta coordination catalyst are heated above their decomposition point in the presence of excess monomer. A controlled, selective opening of the ring with the strained olefin occurs to form a linear, soluble polymer chain having the non-polymerized group pendant from the chain. Unstrained olefins are virtually unaffected as are oxygen containing ether groups.

These and many other features and attendant advantages of the invention will become apparent as the invention becomes better understood by reference to the following detailed description.

DETAILED DESCRIPTION OF THE INVENTION

In the polymerization system of the invention an active catalyst is formed by first reacting a unit of monomer of the formula:

      (1)

where Z is a homocarbon or heterocarbon linkage containing from 2 to 6 chain atoms and Y is a group polymerizable with Lewis acids or transition metal salt coordination catalysts such as unstrained cyclic olefin bond or an oxygen containing functional group such as an ether group with a source of $Cp_2TiCH_2$-according to the following reaction:

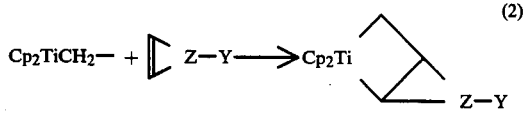      (2)

The active catalyst (2) reacts with excess monomer to form a polymer having the following repeating unit:

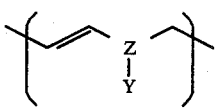
(3)

Precursor sources of Cp$_2$TiCH$_2$— can be the Tebbe reagent:

(4)

or

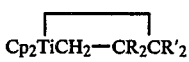
(5)

where R and R$^1$ are selected from lower alkyl of 1 to 6 carbon atoms, monocyclic aryl such as phenyl, lower alkoxy of 1 to 6 carbon atoms, or hydrogen and Cp is $\eta^5$—C$_5$H$_5$.

The monomer can be a diolefin such as endodicyclopentadiene or an unsaturated ring-ether containing monomers such as 7-oxo-norbornenes.

Polymerization is effected by forming a mixture of catalyst reagent and excess monomer and heating the mixture to the decomposition temperature at which ring-opening occurs usually above 50° C. At high temperatures, thermal cross-linking may occur for certain monomers. In the case of endo-dicyclopentadiene, total yield increases but soluble fraction is substantially reduced at polymerization temperatures near 80° C.

Polymerization with the Tebbe reagent is usually conducted in presence of pyridine. However, the catalyst eliminates AlR$_2$Cl during polymerization which is soluble in the catalyst solvent. In an improved catalyst preparation method according to the invention, the catalyst preparation is conducted with a base that forms an insoluble adduct with AlR$_2$Cl such as 4-dimethylaminopyridine (DMAP) or tetramethylenetetramine (TMTA). The Tebbe reagent is mixed with a stoichiometric amount of the base and an excess of monomer in inert solvent such as benzene, toluene, or methylene chloride. The solution is stirred at ambient then cooled substantially below ambient. Addition of an aliphatic solvent such as pentane results in precipitation of the base-AlR$_2$Cl adduct. The supernatant catalyst solution is filtered and concentrated with reduced pressure.

Another and preferred method of preparing the catalyst is to eliminate aluminum by using compound (5). Compound (5) when reacted with monomer in solution with stirring at room temperature forming the titanacyclobutane catalyst by elimination of volatile component (isobutylene when R$^1$ is Me and R is H) which is removed by venting.

Experiments were conducted according to the following general procedure. All operations were carried out either in an inert atmosphere dry box or on a vacuum line using standard Schlenk techniques. Benzene was degassed and dried over sodium benzophenone-ketyl prior to vacuum transfer and use. $\eta$-Pentane was freed from olefins using standard procedures. It was then degassed and dried over sodium benzophenone-ketyl prior to vacuum transfer and use. Methanol was degassed prior to use.

(6)

and

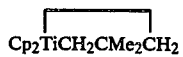
(7)

were prepared according to established procedures (K. Ott, D. Straus, Ph.D. Theses, California Institute of Technology, 1983). Endo-dicyclopentadiene (Wiley Organics) was used without further purification. 7-Oxo-1,4-dihydronapthalene was prepared according to literature procedures (*Can. J. Chem.*, 1965, 43, 1599; *J. Org. Chem.*, 1969, 34, 3089). 4-Dimethylaminopyridine (Aldrich) was recrystallized from toluene.

NMR spectra was recorded on a JEOL FX-90Q (89.60 MHz $^1$H, 22.53 MHz $^{13}$C) instrument. IR spectra were recorded on a Beckman 4240 spectrophotometer. Polymer molecular weight distributions were determined using a Waters Model 4000 HPLC.

EXAMPLE 1

(A) Catalyst Preparation. To 30 mg (0.12 mmol) of compound 7 was added 2 mL of a solution of 20% endo-cyclopentadiene in benzene (2.8 mmol). The mixture was stirred at 23° C. for 15 min with occasional venting to remove isobutylene produced.

(B) Polymerization. The catalyst solution was heated to 65° C. over 2 h and maintained at 65° C. for an additional 10 h.

(C) Workup. After cooling to 23° C., the solution was added dropwise to excess rapidly-stirred methanol. The resulting precipitated polymer was collected by centrifugation and dried under reduced pressure. Yields vary from 30–60% based on initial monomer. Solubilities (in C$_6$H$_6$) vary from 50–80%.

(D) Polymer Characterization. IR, $^1$H NMR, and $^{13}$C NMR spectra were obtained. No signals attributable to a bicyclic double bond remain. HPLC analysis of the CH$_2$Cl$_2$-soluble polymer yields an average molecular weight of 5,000.

EXAMPLE 2

Example 1 was repeated but the reaction time was increased from 12 to 24 h. This does not appreciably increase the yield.

EXAMPLE 3

Example 1 was repeated except the polymerization temperature was increased from 65° C. to 78° C. This greatly increased the yeild; however, the resulting polymer was less than 10% soluble.

The polymer produced in Examples 1–3 degrade to an insoluble tan powder on prolonged exposure to air.

EXAMPLE 4

(A) Catalyst Preparation. To 50 mg (0.18 mmol) of compound 6 was added 0.25 mL of a 20% solution of endo-cyclopentadiene in benzene (0.4 mmol) and 25 mg (0.2 mmol) 4-dimethylaminopyridine (DMAP). The solution was stirred 15 min, then cooled to −40° C. Addition of 5 mL pentane resulted in precipitation of the DMAP-AlMe$_2$Cl adduct. The catalyst-containing supernatant was filtered away and concentrated under reduced pressure.

(B) Polymerization. 2 mL of a 20% solution of endo-cyclopentadiene in benzene (2.8 mmol) was added to the catalyst. The solution was warmed to 65° C. over 2 h and maintained at 65° C. for an additional 10 h.

(C) Workup. The same workup as in Example 1 was utilized. Yield: approximately 5–10%. Solubility: same as above.

(D) Polymer Characterization. The polymer was characterized by its ¹H NMR spectrum.

The low yield resulting from this method of polymer preparation is due to incomplete precipitation of the DMAP-AlMe₂Cl adduct during catalyst preparation. Presumably the yields could be increased to those reported in Example 1, with more complete purification of the catalyst (for example, recrystallization).

EXAMPLE 5

(A) Catalyst Preparation. To 35 mg (0.14 mmol) of compound 7 was added a solution of 0.4 g 7-oxo-1,4-dihydronapthalene dissolved in 2 mL benzene. The solution was stirred at 23° C. for 15 min with occasional venting to remove isobutylene produced.

(B) Polymerization. The catalyst solution was heated to 68° C. over 2 h and maintained at 65° C. for an additional 10 h.

(C) Workup. After cooling to 23° C., polymer was precipitated by addition of 20 mL methanol, collected by centrifugation and dried under reduced pressure. The yield was 45% based on monomer.

(D) Polymer Characterization. IR, ¹H, and ¹³C NMR spectra were obtained. Degrative ozonolysis followed by a reductive workup gives the same product for the polymer as for the monomer. HPLC analysis of the CH₂Cl₂-soluble polymer suggest a low average molecular weight.

The polymer derived from dicyclopentadiene is believed to have this structure:

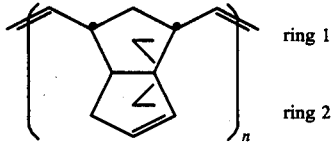

No specific stereochemistry of the acyclic double bonds is implied. Ring 2 is probably endo although some isomerization to the exo form may have occurred. No stereoregularity with respect to the position of the cyclic double bond in adjacent monomer units is implied. The acyclic substituents of ring 1 are cis. NOTE: There is a possibility that some crosslinking i.e., polymerization with ring (2) has occurred.

The catalyst is believed to be a mixture of some or all of the possible structures listed below. Different stereoisomers of these structures may be present as well.

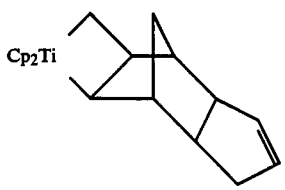

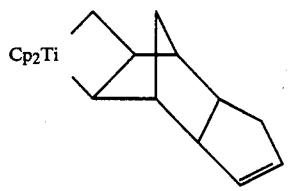

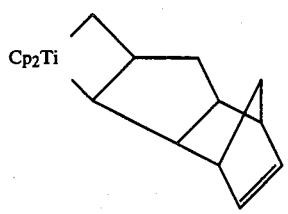

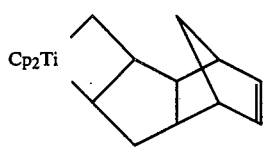

On warming those species having structural types (3) and (4) equilibrate to types (1) or (2) prior to polymerization.

The polymer derived from 7-oxo-1,4-dihydronapthalene is believed to have this structure:

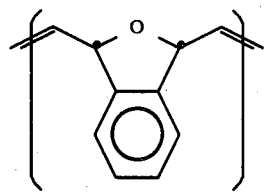

No specific stereochemistry of the double bonds is implied. The acyclic substituents of the oxygen-containing ring are cis.

The catalyst is believed to have the following structure:

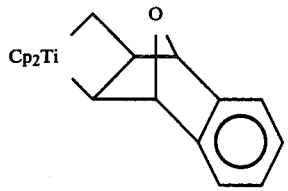

It is to be realized that only preferred embodiments of the invention have been described and that numerous substitutions, modifications and alterations are permissible without departing from the spirit and scope of the invention as defined in the following claims.

We claim:

1. A method of polymerizing comprising reacting a monomer of the formula:

where Z is a hydrocarbon or heterocarbon linkage containing 2 to 6 carbon atoms within a strained ring and Y contains a group polymerizable by a Lewis acid or by a transition metal catalyst but not polymerizable by the present catalyst, with a source of:

to form a titanacyclobutane complex catalyst of the formula:

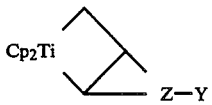

adding an excess of said monomer to the complex; and polymerizing the monomer by selectively and controllably opening the ring containing the strained olefin without polymerizing the other group to form a polymer having a repeating unit of the formula:

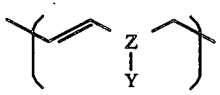

2. A method according to claim 1 in which the group contained in Y is selected from an olefin contained in an unstrained ring or an ether group.

3. A method according to claim 1 in which said source is selected from compounds of the formula:

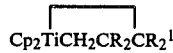

where R and $R^1$ are selected from alkyl of 1 to 6 carbon atoms, monocyclic aryl, alkoxy of 1 to 6 carbon atoms, or hydrogen.

4. A method according to claim 3 in which $R^1$ is methyl and R is H.

5. A method according to claim 3 in which the source is a mixture of a base and a compound of the formula:

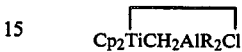

6. A method according to claim 5 in which R is methyl.

7. A method according to claim 5 in which the base forms an insoluble adduct with $AlR_2Cl$.

8. A method according to claim 7 in which the base is selected from dimethylaminopyridine or tetramethylenetetramine.

9. A method according to claim 2 in which the ring containing an unstrained olefin is dicyclopentadiene.

10. A method according to claim 2 in which the ring containing an ether group is a residue of 7-oxo-1, 4-dihydronaphthalene.

11. A method according to claim 9 in which the polymerization temperature is from about 50° C. to about 80° C.

12. A method according to claim 1 in which the polymer has a solubility exceeding 40% by weight.

* * * * *

UNITED STATES PATENT AND TRADEMARK OFFICE
CERTIFICATE OF CORRECTION

PATENT NO.  : 4,690,992
DATED       : September 1, 1987
INVENTOR(S) : Robert H. Grubbs et al It is certified that error appears in the above-identified patent and that said Letters Patent are hereby corrected as shown below:

Column 1, line 55, correct spelling of "Dicyclopentadiene".

Column 4, line 56, correct spelling of "yield".

Column 5, after line 40, correct formula as follows:

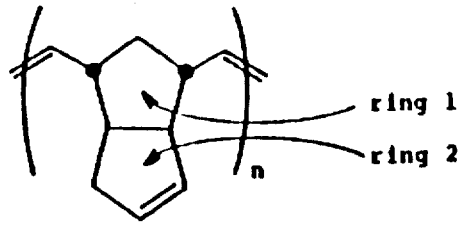

Signed and Sealed this

Nineteenth Day of January, 1988

*Attest:*

DONALD J. QUIGG

*Attesting Officer*         *Commissioner of Patents and Trademarks*